United States Patent [19]

Herkenrath

[11] 4,070,364

[45] Jan. 24, 1978

[54] PROCESS FOR THE PRODUCTION OF [2-ACETOACETYL-AMINOTHIAZOLYL-(4)-]-ACETIC ACID ETHYL ESTER

[75] Inventor: Erik Herkenrath, Glis, Switzerland

[73] Assignee: Lonza, Ltd., Gampel, Switzerland

[21] Appl. No.: 722,874

[22] Filed: Sept. 13, 1976

Related U.S. Application Data

[63] Continuation-in-part of Ser. No. 531,765, Dec. 11, 1974, abandoned.

[30] Foreign Application Priority Data

Dec. 11, 1973   Switzerland ..................... 017303/73

[51] Int. Cl.$^2$ ............................................ C07D 277/56
[52] U.S. Cl. .................................. 260/306.8 R; 71/90
[58] Field of Search ................................. 260/306.8 R

[56] References Cited

PUBLICATIONS

Williams et al., *Org. Syntheses,* 21, pp. 4–5, (1941).
Wagner et al., *Synthetic Org. Chemistry,* John Wiley & Sons, N.Y., 1953, p. 571.

*Primary Examiner*—R. Gallagher
*Attorney, Agent, or Firm*—Virgil H. Marsh

[57] ABSTRACT

The process for the production of [2-acetoacetylaminothiazolyl-(4)-]-acetic acid ethyl ester. The process involves reacting [2-aminothiazolyl-(4)-]-acetic acid ethyl ester with diketene in an organic solvent in the presence of 5 to 15 percent of glacial acetic acid, based on the amount of the solvent, at a temperature between 30° and 80° C.

5 Claims, No Drawings

PROCESS FOR THE PRODUCTION OF [2-ACETOACETYL-AMINOTHIAZOLYL-(4)-]-ACETIC ACID ETHYL ESTER

This is a continuation-in-part of U.S. application Ser. No. 531,765, filed on Dec. 11, 1974 now abandoned.

BACKGROUND OF THIS INVENTION

1. Field of This Invention

This invention relates to a process for the production of [2-acetoacetylaminothiazolyl-(4)-]-acetic acid ethyl ester.

2. Prior Art

Attention is drawn to Wagner et al., Synthetic Org. Chemistry, John Wiley & Sons, N.Y., (1953), p. 571.

BROAD DESCRIPTION OF THIS INVENTION

An object of this invention is to provide a process for the production of [2-acetoacetylaminothiazolyl-(4)-]-acetic acid ethyl ester. Other objects and advantages are set out herein or are obvious herefrom to one ordinarily skilled in the art.

Such objects and advantages are achieved by the process of this invention.

This invention includes a process for the production of [2-acetoacetylaminothiazolyl-(4)-]-acetic acid ethyl ester. The process includes reacting [2-aminothiazolyl-(4)-]-acetic acid ethyl ester with diketene in an organic solvent in the presence of 5 to 15 percent of glacial acetic acid, based on the amount of said solvent, at a temperature between 30° and 80° C.

The [2-acetoacetylaminothiazolyl-(4)-]-acetic acid ethyl ester, obtainable according to this invention, is an intermediate for the production of color pigments and is effective as a photopolymerization initiator. Furthermore, applicant has found that it has growth-controlling characteristics (a plant growth regulator).

DETAILED DESCRIPTION OF THIS INVENTION

The reaction temperature should be between 30° and 80° C. and preferably is between 50° and 60° C.

It is important that the reaction is conducted in the presence of a small amount of glacial acetic acid. So preferably glacial acetic acid is used in an amount between 5 and 15 percent by weight (and most preferably between 8 and 12 percent by weight) based on the amount of solvent. The weight ratio of the glacial acetic acid to diketene should be between 1:200 and 1:3,000.

The starting material [2-aminothiazolyl-(4)-]-acetic acid ethyl ester can be prepared by reaction of γ-chloroacetic acid ethyl ester with thiourea (see Beilstein Hw 3, 663, and Beilstein Hw 27, 336).

Any organic solvent can be used. But best results are obtained when a low acetic acid ester, e.g., an alkyl acetate (having 1 to 4 carbon atoms in the alkyl group, i.e., alkyl ester radical), or a aromatic hydrocarbon or a halogenated hydrocarbon is used as the solvent, so such solvents are preferred. The most preferred solvent is butyl acetate. Mixtures of organic solvents can be used. Examples of useful alkyl acetate solvents are methyl acetate, ethyl acetate, isopropyl acetate, propyl acetate, butyl acetate, isobutyl acetate, sec. butyl acetate, and tert. butyl acetate. Examples of useful aromatic hydrocarbon solvents are benzene, toluene, ethyl benzene, o-xylene, 1,3,5-trimethyl benzene, pentyl benzene, m-xylene, 1,2,4-trimethyl benzene, propyl benzene, p-xylene, 1,2,3-trimethyl benzene, isopropyl benzene, 1,2,3,4-tetramethyl benzene, butyl benzene, 1,2,3,5-tetramethyl benzene, isobutyl benzene, 1,2,4,5-tetramethyl benzene, 1,2-diethyl benzene, 1-methyl-3-propyl benzene, 1,3-diethyl benzene, 1-methyl-2-propyl benzene, 1,4-diethyl benzene, 1-methyl-4-propyl benzene, 1,2-dimethyl-4-ethyl benzene, 1,3-dimethyl-5-ethyl benzene, 1,4-dimethyl-2-ethyl benzene and 2,4-dimethyl-1-ethyl benzene. Examples of useful haloginated hydrocarbon solvents (1 to 4 carbon atoms) are carbon tetrachloride, 1,2-dichloro ethane, 1,2-dibromo ethane, 1,1-dibromo ethane, 1,1-dichloro ethane, 1-bromo-1-chloro ethane, 1,2-dibromo-1,1-dichloro ethane, 1,2-dibromo-1,2-dichloro ethane, 1,2-dibromo propane, 1-iodo propane, 1,3-dibromo propane, 2-iodo propane, 1,2-dichloro propane, 1,1,1,2-tetrachloro propane, 2,2-dichloro propane, 1,2,3-tribromo propane, 1-bromo propane, 1,2,3-trichloro propane, dibromo methane, dibromoiodo methane, diiodofluoro methane, tribromo methane, 1-bromo butane, 1,4-dibromo butane, 2-bromo butane, 1-bromo butane, 1-iodo butane, 2-iodo butane, 2,3-dibromo butane, 1,4-dichloro butane, 2,2-dichloro butane, 2,3-dichloro butane, 1,4-dichloro butane, 1,2,2,3-tetrachloro butane and 2,2,3-tribromo butane. Examples of other useful organic solvents are amyl acetate, isopropyl cyclopentane, ethyl cyclopentane and propyl cyclopentane.

As used herein all parts, percentages, ratios and proportions are on a weight basis unless otherwise stated or obvious to one ordinarily skilled in the art.

EXAMPLE 1

18.6 gm. of [2-aminothiazolyl-(4)-]-acetic acid ethyl ester, dissolved in 50 ml of butyl acetate and 5 ml of glacial acetic acid, were placed in a 250 ml 3-necked flask, equipped with an agitator, a reflux cooler and a thermometer, as well as with an electric heating jacket, and were heated to 50° C. with stirring. After that, while the temperature rose to 50° C., 8.7 gm. of diketene were added drop by drop. After completion of the addition of diketene, the temperature was maintained at 55° to 60° C. and the reaction mixture stirred for 2 hours. After cooling, crystals developed and were filtered off. The mother lye was concentrated and the further crystals obtained thereby were isolated. After washing and drying in a vacuum at 60° to 70° C, 22.8 gm. of the desired product were obtained. That corresponded to a yield of 84.4 percent, based on the aminothiazol used.

The pure [2-acetoacetylaminothiazolyl-(4)-]-acetic acid ethyl ester had a melting point of 133° to 135° C. The elementary analysis of the product was $C_{11}H_{14}N_2O_4S$, and the product has a molecular weight of 270. The following is further data on the product:

|  | C | H | N | S |
|---|---|---|---|---|
| Found: | 48.1% | 5.1% | 10.1% | 13.1% |
| Calculated | 48.87% | 5.23% | 10.37% | 11.86% |

EXAMPLES 2 AND 3

Example 1 was repeated twice, except that in place of butyl acetate, toluene or carbon tetrachloride was used. Yields of 76.3 percent and 71.5 percent, respectively, were obtained.

EXAMPLE 4

The growth substance activity of [2-acetoacetylaminothiazolyl-(4)-]-acetic acid ethyl ester was found as follows:

Grains of wheat were made to germinate on filter paper in an incubator in the dark at 24° C. When the small germs were 25 to 35 mm long, coleoptile pieces of 9 mm length were removed approximately 3 to 5 mm from the point were cut off and were placed into distilled water for 2 hours. After that the coleoptile pieces were in Petri dishes with test solvents. The growth in length was determined after 24 hours, whereby, as a control, distilled water and, as a comparison substance, indoleacetic acid was used.

| Concentration in Mole | $1 \times 10^{-3}$ | $1 \times 10^{-4}$ | $1 \times 10^{-5}$ |
|---|---|---|---|
| [2-acetoacetylaminothiazolyl-(4)-]-acetic acid ethyl ester | 114 | 114 | 109 |
| Indoleacetic acid | 91 | 120 | 125 |

The growth in length of the control (distilled water) was assumed to be 100.

EXAMPLE 5

18.6 gm. of [2-aminothiazolyl-(4)-]-acetic acid ethyl ester, dissolved in 50 ml of butyl acetate and 5 ml of glacial acetic acid, were placed in a 250 ml 3-necked flask, equipped with an agitator, a reflux cooler and a thermometer, as well as with an electric heating jacket, and were heated to 50° C. with stirring. A homogenous solution was obtained. After that, while the temperature rose from 50° to 60° C., 8.7 gm. of diketene were added drop by drop. After completion of the addition of diketene, the temperature was maintained at 55° to 60° C. and the reaction mixture stirred for 2 hours. After cooling, crystals developed and were filtered off. The precipitation began when cooling caused the solution temperature to reach 50° C. The mother lye was concentrated and the further crystals obtained thereby were isolated. After washing and drying in a vacuum at 60° to 70° C, 19.2 gm. of the product were obtained. The resultant [2-acetoacetylaminothiazolyl-(4)-]-acetic acid ethyl ester had a melting point of 132.6° to 133.0° C.

COMPARISON EXAMPLE A 18.6 gm. of [2-aminothiazolyl-(4)-]-acetic acid ethyl ester, dissolved in 50 ml of butyl acetate, were placed in a 250 ml 3-necked flask, equipped with an agitator, a reflux cooler and a thermometer, as well as with an electric heating jacket, and were heated to 50° C. with stirring. No homogenous solution was obtained. After that, 8.7 gm. of diketene were added drop by drop. There was no temperature rise during the diketene addition and reaction (as found by experience) — so, after completion of the addition of diketene, the temperature was raised to 55° C. by external heating. The temperature was maintained at 55° to 60° C and the reaction mixture stirred for 2 hours. After cooling, crystals developed and were filtered off. Precipitation did not begin until cooling had caused the solution temperature to reach 40° C. The mother lye was concentrated and the further crystals obtained thereby were isolated. After washing and drying in a vacuum at 60° to 70° C, 18.8 gm. of the desired product were obtained. The resultant [2-acetoacetylaminothiazolyl-(4)-]-acetic acid ethyl ester had a melting point of 111.7° to 112.0° C.

No glacial acetic acid was used in Comparison Example A and a very impure product was obtained. Glacial acetic acid was used in Example 5 and a very pure product was obtained. Example 5 represents this invention. The product of Example 5 had a melting point of 132.6° to 133.0° C. and the product of Comparison Example A had a melting point of only 111.7° to 112.0° C. The much higher melting point of the product of Comparison Example 5 indicates a much higher degree of purity (than the product of Comparison Example A). The product of Comparison Example A, produced without glacial acetic acid addition, was apparently contaminated by unconverted starting material, which also shows a lower degree of conversion (or reaction).

Example 5 and Comparison Example A clearly establish that in order to obtain [2-acetoacetylaminothiazolyl-(4)]-acetic acid ester of essentially pure quality, it is critical and indispensible that a small quantity of glacial acetic acid be added to the solvent. This addition of glacial acetic acid is necessary for the following reasons:

1. The glacial acetic acid exercises a catalytic influence on the conversion of the starting [2-aminothiazolyl-(4)-]-acetic acid ester with diketene; and
2. The starting [2-aminothiazolyl-(4)]-acetic acid ester will start to dissolve completely only when glacial acetic acid is added — such dissolution will start even prior to the addition of the diketene when glacial acetic acid is added.

It is noted that in the case of Example 5, having glacial acetic acid addition, that a homogeneous solution was available after heating the solution to 50° C. (prior to the addition of diketene), but that no such homogeneous solution was available in the case of Comparison Example A (having no glacial acetic acid addition). When glacial acetic acid was present, a temperature increase (due to reaction heat), which was not observed in the case of the example not having any addition of glacial acetic acid, occurred even without exterior heat action. Also, in the case of Example 5 which has glacial acetic acid present, the newly formed product began to precipitate at 50° C., but in the case of Comparison Example A which is without glacial acetic acid, precipitation occurred only after cooling to 40° C.

Both Example 5 and Comparison Example A used a slight molar excess of diketene (1 mole of [2-aminothiazolyl-(4)-]-acetic acid ester to 1.04 moles of diketene).

Comparison of Example 5 and Comparison Example A clearly shows the critical nature of the glacial acetic acid addition.

What is claimed is:

1. The process for the production of [2-acetoacetylaminothiazolyl-(4)-]-acetic acid ethyl ester which comprises reacting [2-aminothiazolyl-(4)-]-acetic acid ethyl ester with diketene in an organic solvent in the presence of 5 to 15 percent of glacial acetic acid, based on the amount of said solvent, at a temperature between 30° and 80° C., said solvent being selected from the group consisting of an alkyl acetate having 1 to 4 carbon atoms in the alkyl group, an aromatic hydrocarbon, a halogenated hydrocarbon having 1 to 4 carbon atoms, amyl acetate, isopropyl cyclopentane, ethyl cyclopentane and propyl cyclopentane.

2. The process of claim 1 wherein the reaction is conducted at a temperature between 50° and 60° C.

3. The process of claim 1 wherein said glacian acetic acid is present in an amount between 8 and 12 percent, based on said organic solvent.

4. The process of claim 1 wherein said solvent is an aromatic hydrocarbon selected from the group consisting of benzene, toluene, ethyl benzene, o-xylene, 1,3,5-trimethyl benzene, pentyl benzene, m-xylene, 1,2,4-trimethyl benzene, propyl benzene, p-xylene, 1,2,3-trimethyl benzene, isopropyl benzene, 1,2,3,4-tetramethyl benzene, butyl benzene, 1,2,3,5-tetramethyl benzene, isobutyl benzene, 1,2,4,5-tetramethyl benzene, 1,2-diethyl benzene, 1-methyl-3-propyl benzene, 1,3-diethyl benzene, 1-methyl-2-propyl benzene, 1-4-diethyl benzene, 1-methyl-4-propyl benzene, 1,2-dimethyl-4-ethyl benzene, 1,3-dimethyl-5-ethyl benzene, 1,4-dimethyl-2-ethyl benzene and 2,4-dimethyl-1-ethyl benzene.

5. The process of claim 1 wherein said solvent is a halogenated hydrocarbon selected from the group consisting of carbon tetrachloride, 1,2-dichloro ethane, 1,2-dibromo ethane, 1,1-dibromo ethane, 1,1-dichloro ethane, 1-bromo-1-chloro ethane, 1,2-dibromo-1,1-dichloro ethane, 1,2-dibromo-1,2-dichloro ethane, 1,2-dibromo propane, 1-iodo propane, 1,3-dibromo-propane, 2-iodo propane, 1,2-dichloro propane, 1,1,1,2-tetrachloro propane, 2,2-dichloro propane, 1,2,3-tribromo propane, 1-bromo propane, 1,2,3-trichloro propane, dibromo methane, dibromoiodo methane, diiodofluoro methane, tribromo methane, 1-bromo butane, 1,4-dibromo butane, 2-bromo butane, 1-bromo butane, 1-iodo butane, 2-iodo butane, 2,3-dibromo butane, 1,4-dichloro butane, 2,2-dichloro butane, 2,3-dichloro butane, 1,4-dichloro butane, 1,2,2,3-tetrachloro butane and 2,2,3-tribromo butane.

* * * * *